US011266773B2

(12) United States Patent
Garrido et al.

(10) Patent No.: US 11,266,773 B2
(45) Date of Patent: Mar. 8, 2022

(54) FLUID LEAK DETECTION IN A DIALYSIS MACHINE

(71) Applicant: Fresenius Medical Care Holdings, Inc., Waltham, MA (US)

(72) Inventors: Hernando Garrido, Concord, CA (US); Anthony T. Ortega, Antioch, CA (US); Asif A. Khan, Hercules, CA (US); John A. Biewer, Benicia, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 0 days.

(21) Appl. No.: 17/113,203

(22) Filed: Dec. 7, 2020

(65) Prior Publication Data

US 2021/0113759 A1 Apr. 22, 2021

Related U.S. Application Data

(63) Continuation of application No. 16/839,533, filed on Apr. 3, 2020, now Pat. No. 10,888,649, which is a continuation of application No. 15/647,097, filed on Jul. 11, 2017, now Pat. No. 10,682,455.

(51) Int. Cl.
| | |
|---|---|
| *G01M 3/16* | (2006.01) |
| *A61M 1/36* | (2006.01) |
| *A61M 1/28* | (2006.01) |
| *A61M 1/34* | (2006.01) |
| *A61M 1/14* | (2006.01) |
| *G08B 7/06* | (2006.01) |

(52) U.S. Cl.
CPC ............ *A61M 1/3669* (2013.01); *A61M 1/14* (2013.01); *A61M 1/28* (2013.01); *A61M 1/34* (2013.01); *G01M 3/16* (2013.01); *G08B 7/06* (2013.01); *A61M 2205/12* (2013.01); *A61M 2205/15* (2013.01); *A61M 2205/18* (2013.01); *A61M 2205/3317* (2013.01); *A61M 2205/502* (2013.01); *A61M 2205/581* (2013.01); *A61M 2205/583* (2013.01)

(58) Field of Classification Search
CPC combination set(s) only.
See application file for complete search history.

(56) References Cited

U.S. PATENT DOCUMENTS

| | | | |
|---|---|---|---|
| 7,641,612 B1 | 1/2010 | McCall | |
| 2004/0127841 A1 | 7/2004 | Briggs | |
| 2009/0322543 A1* | 12/2009 | Crnkovich | ............ A61M 1/367 340/604 |

(Continued)

FOREIGN PATENT DOCUMENTS

| | | |
|---|---|---|
| CN | 104394899 A | 3/2015 |
| WO | 2015130906 A1 | 9/2015 |

*Primary Examiner* — Xin Y Zhong
(74) *Attorney, Agent, or Firm* — Kacvinsky Daisak Bluni PLLC (57) ABSTRACT

A dialysis machine (e.g., a peritoneal dialysis machine) may include a housing. The machine may further include a leak detector disposed in the housing, the leak detector being an electrical circuit. In response to fluid contacting the leak detector, a leak in the dialysis machine is detectable. The machine is configured to send a signal based on a short of the electrical circuit from fluid contact with the leak detector to indicate a leak condition.

19 Claims, 11 Drawing Sheets

(56) References Cited

U.S. PATENT DOCUMENTS

| | | | |
|---|---|---|---|
| 2010/0140149 A1* | 6/2010 | Fulkerson | G16H 40/63 210/85 |
| 2014/0251583 A1* | 9/2014 | Eriksen | F28F 3/12 165/104.33 |

* cited by examiner

FLUID LEAK DETECTION IN A DIALYSIS MACHINE

CROSS-REFERENCE TO RELATED APPLICATIONS

The present application is a continuation of U.S. patent application Ser. No. 16/839,533, filed Apr. 3, 2020, entitled "Fluid Leak Detection in a Dialysis Machine," which is a continuation of U.S. patent application Ser. No. 15/647,097, filed Jul. 11, 2017, now U.S. Pat. No. 10,682,455, entitled "Fluid Leak Detection in a Dialysis Machine," the contents of each application is expressly incorporated by reference herein.

FIELD OF THE DISCLOSURE

The disclosure generally relates to a dialysis machine, and more particularly to a leak detector in a dialysis machine and a method for detecting a leak in a dialysis machine.

BACKGROUND OF THE INVENTION

Dialysis machines are known for use in the treatment of renal disease. The two principal dialysis methods are hemodialysis (HD) and peritoneal dialysis (PD). During hemodialysis, the patient's blood is passed through a dialyzer of a hemodialysis machine while also passing dialysate through the dialyzer. A semi-permeable membrane in the dialyzer separates the blood from the dialysate within the dialyzer and allows diffusion and osmosis exchanges to take place between the dialysate and the blood stream. During peritoneal dialysis, the patient's peritoneal cavity is periodically infused with dialysate or dialysis solution. The membranous lining of the patient's peritoneum acts as a natural semi-permeable membrane that allows diffusion and osmosis exchanges to take place between the solution and the blood stream. Automated peritoneal dialysis machines, called PD cyclers, are designed to control the entire peritoneal dialysis process so that it can be performed at home, usually overnight without clinical staff in attendance.

A dialysis machine, such as a peritoneal dialysis machine, may include a removable and/or replaceable cartridge attached to one or more fluid lines for pumping fluid to and from a patient. In peritoneal dialysis machines, for example, one or more fluid lines are inserted into an abdomen of a patient for flowing fresh dialysate and removing used dialysate, waste, and excess fluid. As the cartridge facilitates pumping of the fluid, the dialysis machine may monitor fluid delivery, fluid temperature, flow path, and pressure.

The cartridge may be insertable into the dialysis machine and enclosed within the machine during a dialysis operation. At the conclusion of the operation the cartridge may be removed and properly disposed of. The cartridge and accompanying fluid flow lines, valves, and/or connectors may be single use items, which may be damaged prior to use, thereby allowing a leak to occur during operation. Damage or failure of equipment, e.g., failure of a seal, fitting or connector, may also occur during an operation of the machine with a resulting leak developing at the same time. Leaks may form in any of the valves, lines, and the tubing connections of the cartridge. Leaks may also form as a hole, rip, or tear in one or more fluid bags, for example, the warmer bag, which is used to warm the fresh dialysate prior to being pumped into a patient.

When leaks develop and remain undetected in any of the dialysis machine components, leaking fluid may damage the dialysis machine, possibly beyond repair, requiring full replacement. This can be problematic when a patient requires frequent dialysis treatment and needs to obtain an immediate replacement, which can be costly. Additionally, a leak may affect the quality of the fluid flow and the exchange of the dialysate to the patient, potentially affecting a patient's treatment procedure.

It is with respect to these and other considerations that the present improvements may be useful.

SUMMARY

This Summary is provided to introduce a selection of concepts in a simplified form that are further described below in the Detailed Description. This Summary is not intended to necessarily identify key features or essential features of the claimed subject matter, nor is it intended as an aid in determining the scope of the claimed subject matter.

An exemplary embodiment of a dialysis machine in accordance with the present disclosure may include a housing including a cavity and a leak detector disposed in the cavity of the housing, the leak detector being an electrical circuit, wherein in response to fluid contacting the leak detector, a leak in the dialysis machine is detectable. The dialysis machine may be configured to send a signal based on a short of the electrical circuit from fluid contact with the leak detector to indicate a leak condition.

An exemplary embodiment of a method for detecting a leak in a dialysis machine may including operating the dialysis machine and monitoring a leak condition by a leak detector, the leak detector being an electrical circuit disposed in a housing of the dialysis machine, wherein a leak is detectable in response to fluid contacting the electrical circuit. In response to fluid contact with the leak detector, a signal may be sent to indicate a leak condition based on a short of the electrical circuit.

An exemplary embodiment of a dialysis machine may include a housing and a detector disposed within the housing, the detector being an electrical circuit, wherein a presence of a fluid in the housing is detectable in response to the fluid contacting the detector. The dialysis machine may be configured to send a signal based on a short of the electrical circuit from contact of the fluid with the detector.

BRIEF DESCRIPTION OF THE DRAWINGS

By way of example, specific embodiments of the disclosed machine will now be described, with reference to the accompanying drawings, in which.

DETAILED DESCRIPTION

The present embodiments will now be described more fully hereinafter with reference to the accompanying drawings, in which several exemplary embodiments are shown. The subject matter of the present disclosure, however, may be embodied in many different forms and should not be construed as limited to the embodiments set forth herein. Rather, these embodiments are provided so that this disclosure will be thorough and complete, and willfully convey the scope of the subject matter to those skilled in the art. In the drawings, like numbers refer to like elements throughout.

A dialysis machine according to the present invention may be able to quickly detect any leaks that may develop from any of the machine components, or detect any other undesired fluid contact that may result to the machine components, so that operation of the machine may be shut down, thereby ensuring patient safety and limiting or eliminating the potential for damage or further damage to components of the machine that are sensitive to fluid contact, e.g., electrical and electronic components. Dialysis operation is often not able to be monitored manually on a continual basis for leaks or other fluid conditions, or it may not be efficient or practical to do so. This is particularly the case where dialysis is performed while a patient is sleeping, e.g., in the case of peritoneal machines that are often self-administered in the home of a patient. Automatic detection and shutdown is therefore important to prevent any potential machine malfunction or delivery of improper treatment.

Figure 1:
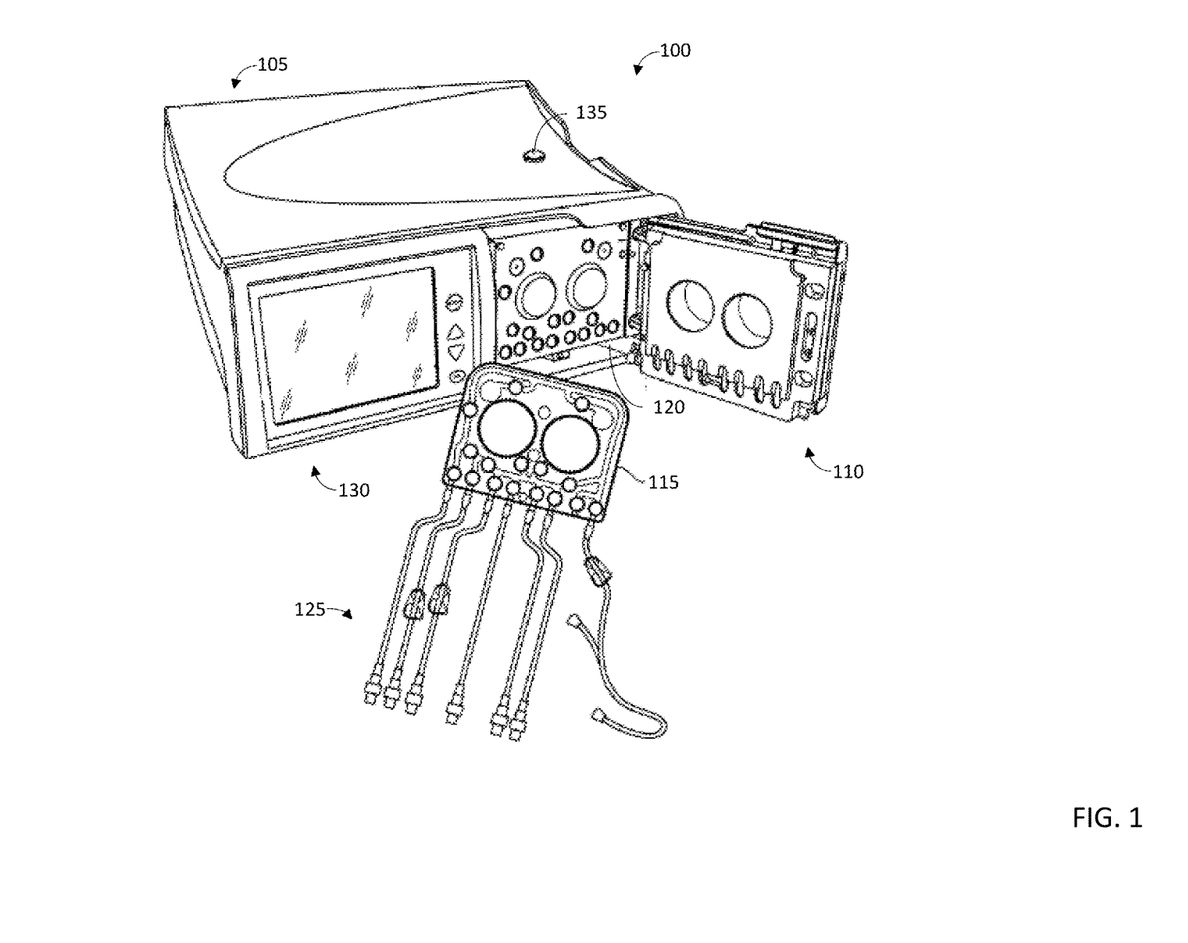
FIG. 1 illustrates an exemplary embodiment of a dialysis machine according to the present disclosure.
Figure 2:
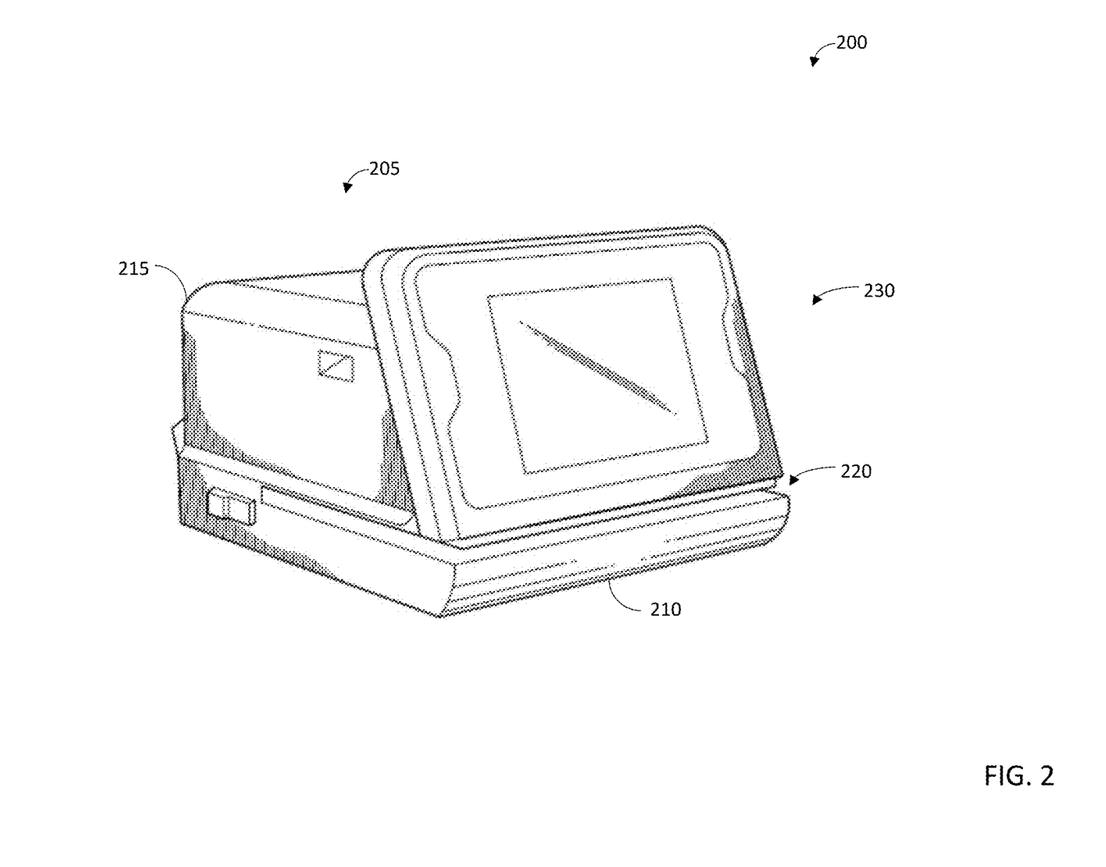
FIG. 2 illustrates another exemplary embodiment of a dialysis machine according to the present disclosure.

Referring to FIG. 1, a dialysis machine 100 according to an embodiment of the present disclosure is shown. The machine 100 may include a housing 105, a door 110 for receiving a cartridge 115 in a cavity 120, and a user interface portion 130. Fluid lines 125 may be coupled to the cartridge in a known manner, such as via a connector, and may further include valves for controlling fluid flow to and from fluid bags including fresh dialysate and warming fluid. In another embodiment, at least a portion of the fluid lines 125 may be integral to the cartridge 115. Prior to operation, a user may open the door 110 to insert a fresh cartridge 115, and to remove the used cartridge 115 after operation.

The cartridge 115 may be placed in the cavity 120 of the machine 100 for operation. During operation, dialysate fluid may be flowed into a patient's abdomen via the cartridge 115, and spent dialysate, waste, and/or excess fluid may be removed from the patient's abdomen via the cartridge 115. The door 110 may be securely closed to the machine 100. Peritoneal dialysis for a patient may include a total treatment of 12 liters of fluid, where 2 liters of dialysate fluid are pumped into a patient's abdomen, held for a period of time, e.g., about an hour, and then pumped out of the patient. This is repeated until the full treatment volume is achieved, and usually occurs overnight while a patient sleeps.

The user interface portion 130 may be a touch screen, and may include one or more buttons for selecting and/or entering user information. The user interface portion 130 may be operatively connected to a controller (not shown) and disposed in the machine 100 for receiving and processing the inputs to operate the dialysis machine 100. A warmer pouch (not shown) may be placed on top of the machine 100, over heater 135. The heater 135 may increase the temperature of fluid in the warmer pouch to approximately a body temperature of the user, e.g., 98°-99° F. In some embodiments, fluid from the warmer pouch may be cycled during operation via the fluid lines 125 and cartridge 115 to increase the temperature of dialysate fluid prior to flowing the dialysate fluid into the patient.

As discussed above, fluid may leak from at least one of the cartridge 115, fluid bags, fluid lines 125, valves, and connections thereof during operation. According to an embodiment of the present disclosure, a leak detector 405 (FIG. 4) may monitor a leak condition, and detect a leak immediately or within a very short time after the leak occurs during operation and signal to the user and/or patient before the machine 100 incurs severe leak damage. If a leak is detected, an alarm condition may be generated, such as a visual and/or audible notifier. In some embodiments, the machine 100 may wirelessly transmit (e.g., via a wireless Internet connection) the alarm condition to a remote location, including but not limited to a doctor's office, hospital, call center, and technical support. For example, the machine 100 may provide real time remote monitoring of machine operation. The machine 100 may include a memory for storing data, or may transmit data to a local or remote server at scheduled intervals.

Figure 3A:
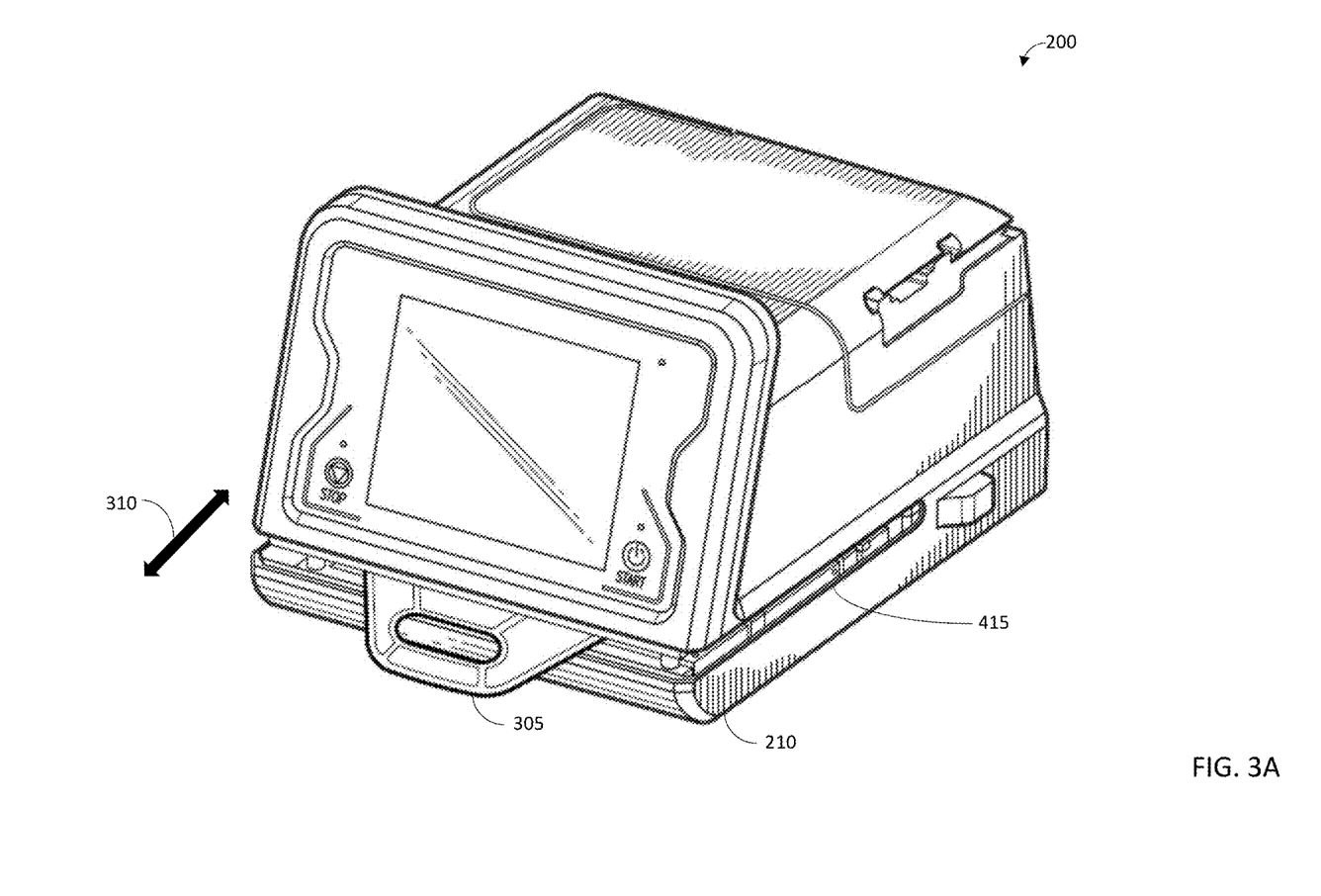
FIGS. 3A-3C illustrate an exemplary embodiment of a fluid bag placement in the dialysis machine of FIG. 2 according to the present disclosure.
Figure 3B:
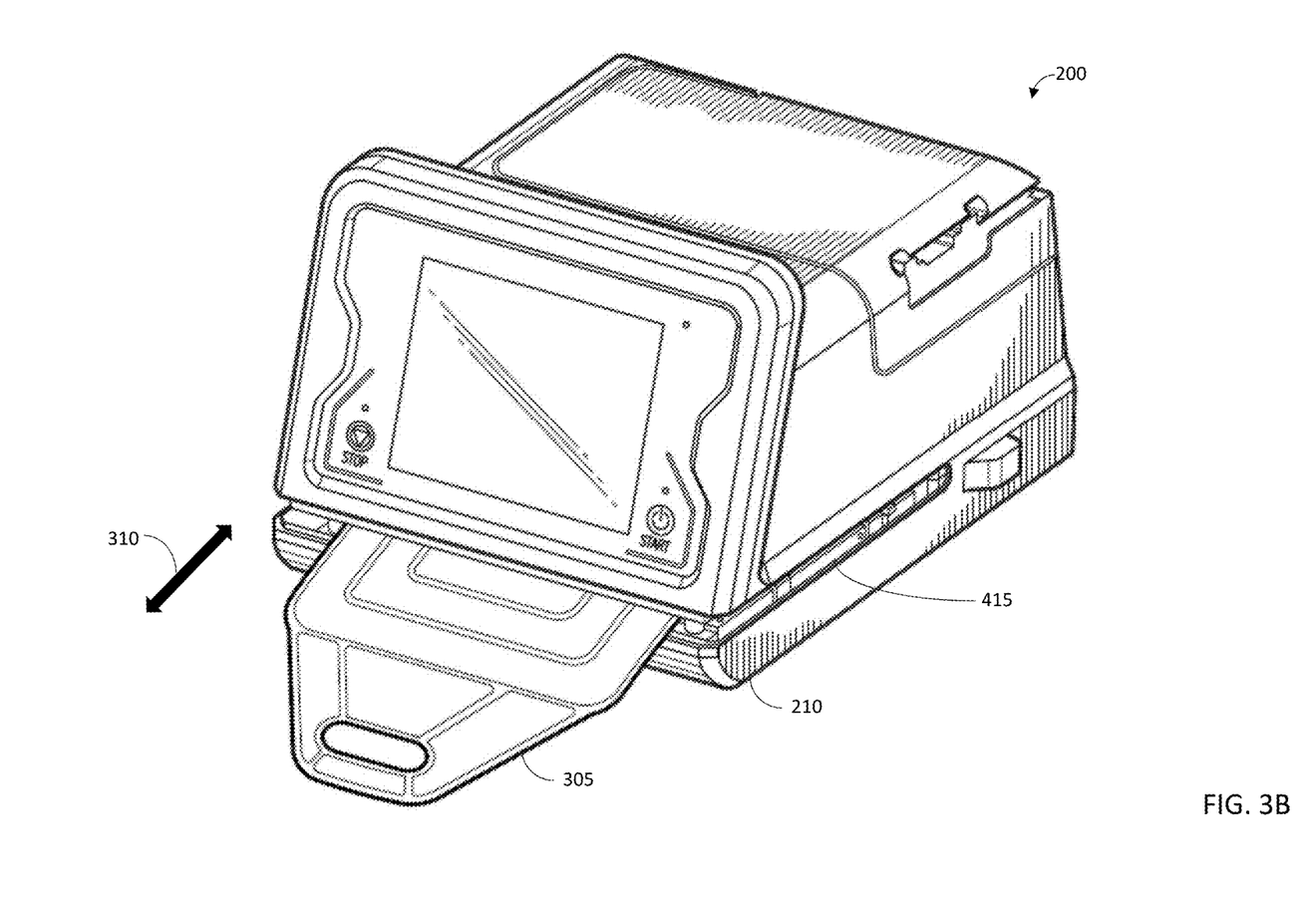
Figure 3C:
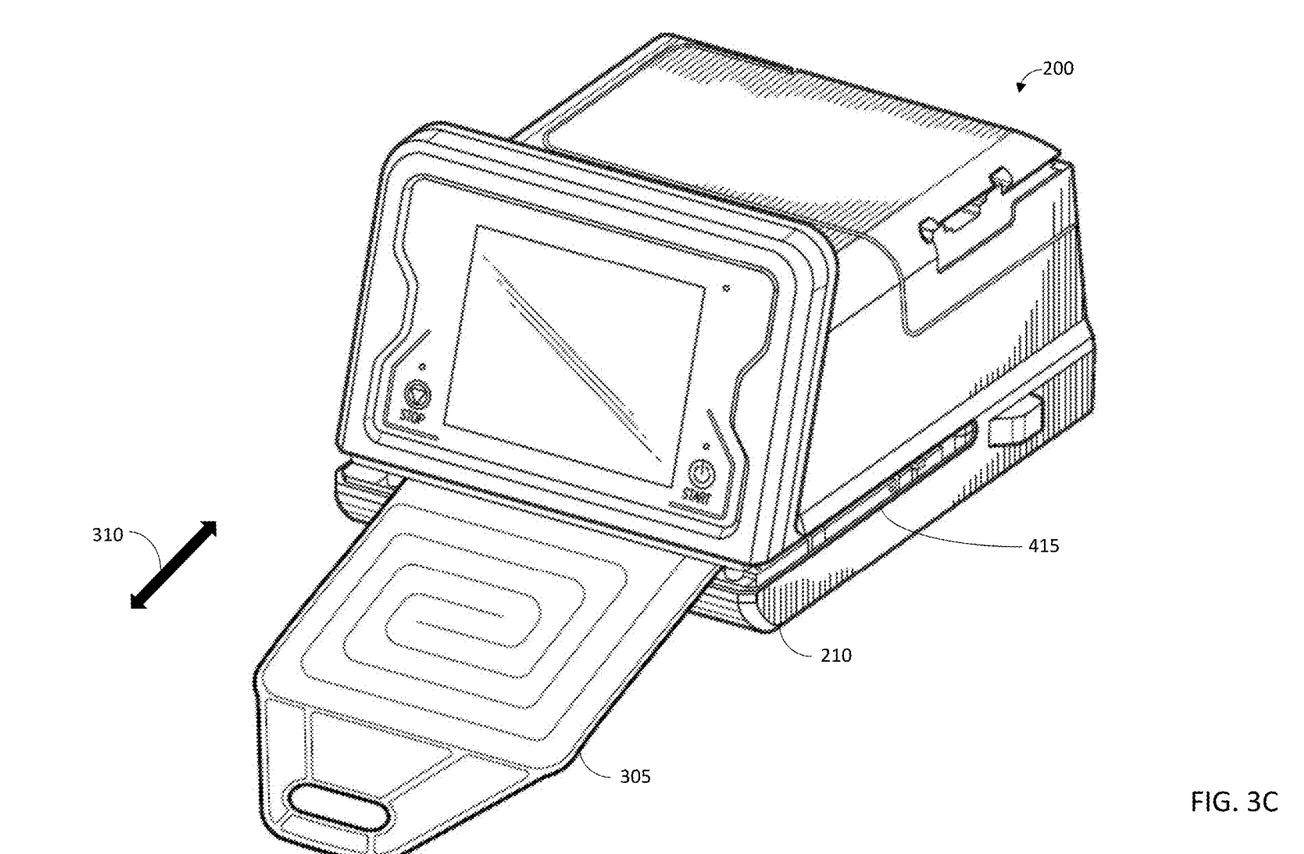

FIGS. 2 and 3A-3C illustrate another exemplary embodiment of a dialysis machine 200 according to the present disclosure. The machine 200 may include a housing 205 and a user interface portion 230. A cartridge (not shown) may similarly be insertable into or associated with the machine 200, e.g., as described above with respect to the machine 100, being connected to one or more fluid bags via the fluid lines 125, and pumping fresh dialysate into the user and removing used dialysate, waste, and/or excess fluid. An opening, or gap 220 may be formed between at least a portion of a lower housing portion 210 and at least a portion of an upper housing portion 215. In some embodiments, the gap 220 may be configured to receive a warmer pouch 305 (FIGS. 3A-3C).

In an embodiment, and as shown in FIGS. 3A-3C, dialysate fluid may be heatable by an internal heating system, such as an internal heating plate and warmer pouch 305 and/or a different internal heating system. When the warmer pouch 305 is inserted into the gap 220 as shown in FIG. 3A, the warmer pouch 305 may be disposed directly above and parallel to the internal heating system of the machine 200. The warmer pouch 305 may be insertable and/or removable from the gap 220 as shown in FIGS. 3A-3C in a direction indicated by arrow 310. A portion of the lower housing portion 210 and/or the leak detector casing 415 may be removed or otherwise allow for visibility of a leak detector 405 as shown in FIGS. 3A-3C. The internal heating system may be disposed in at least a portion of the lower housing portion 210, with the leak detector 405 being disposed around edges of the internal heating system. The leak detector 405 and the leak detector casing 415 may be disposed in the lower housing portion 210 so when the warmer pouch 305 is inserted in the gap 220, any potential fluid leakage may be monitored and detectable by the leak detector 405. It may be advantageous to heat the dialysis fluid in an internal area of the machine 200 to better control the temperature of the fluid. In embodiments where fluid is being heated by an internal system of the machine 200, it is imperative to detect immediately any leaks that may occur to ensure patient safety.

Figure 4:
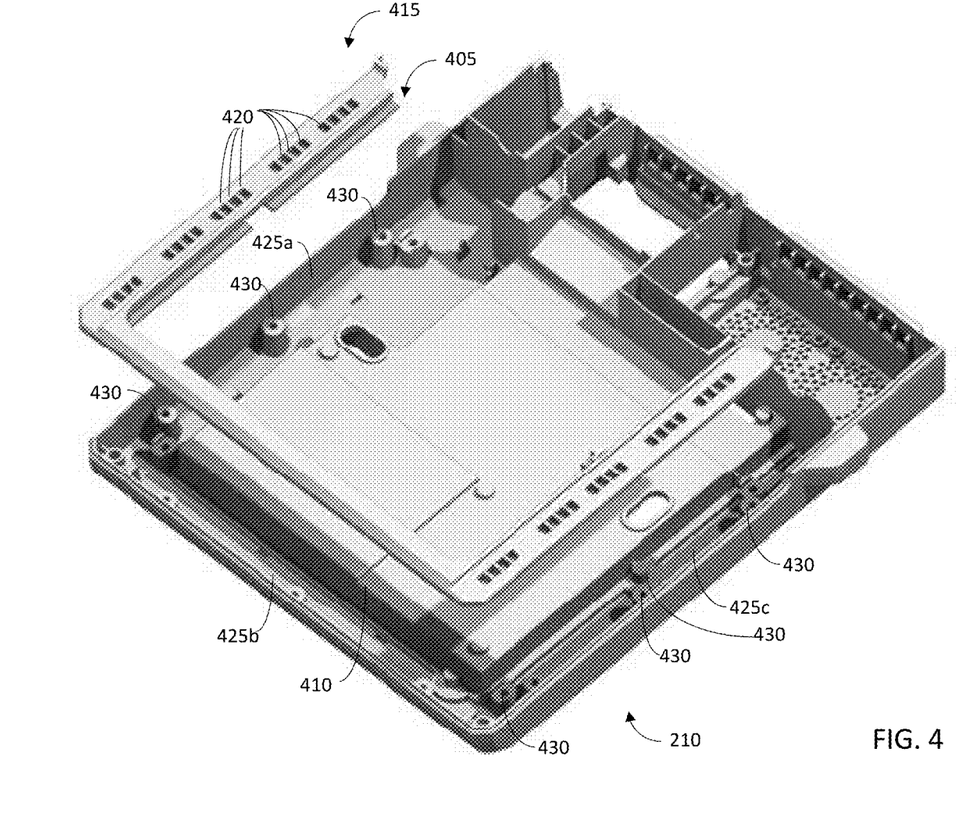
FIG. 4 illustrates a partial exploded view of an exemplary embodiment the dialysis machine of FIGS. 2 and 3A-3C according to the present disclosure.

In embodiments, the housing 105, 205 may be rectangular, although any shape suitable for receiving at least one of a cartridge, fluid bag, and fluid lines may be used. The housing 105, 205 may be made of rigid plastic, metal, composite, or the like, for securely enclosing internal components, including but not limited to a controller, processor, power source, main circuit board, sensors, internal heating system, and at least one of a leak detector 405 (FIG. 4). It is understood that these internal components may be operatively connected to any of each other in a known manner.

According to an exemplary embodiment, a leak detector may be incorporated into the housing of the machines described above to detect leaks from any one or more of a cartridge, fluid lines, and fluid bags, and shut down the machine and operation to ensure patient safety. An exemplary leak detector 405 for the housing 205 of machine 200 is depicted with reference to FIG. 4, which shows a portion of the housing 205, e.g., a lower housing portion 210. The leak detector 405 may be configured to fit within a cavity 410 of the lower housing portion 210 of the housing 205. The leak detector 405 may be an electrical circuit. In some embodiments, the electrical circuit may be at least partially flexible, to allow for bending and/or twisting. For example, the electrical circuit may be a combination of rigid and flexible portions. It may be advantageous to include a flexible circuit as the leak detector 405 to allow for flexure during assembly of the machine 200 and for proper fit with other internal components, e.g., the internal heating system for the warmer pouch 305 in the machine 200. A leak detector configured for machine 100 may be similar in shape to the leak detector 405, and may be configured in accordance with dimensional requirements of the machine 100.

In embodiments, the leak detector 405 may be protected by a leak detector casing 415, the leak detector casing 415 being configured to cover or enclose at least a portion of the leak detector 405. The leak detector 405 may be disposed between the lower housing portion 210 and the leak detector casing 415, so that the leak detector casing 415 covers a top surface of the leak detector 405. The leak detector casing 415 may be formed of a metal, plastic, composite or the like, to provide structural support for the leak detector 405 and to protect the leak detector 405 from other debris and damage while still allowing leaked fluid to contact the leak detector 405. In embodiments, the leak detector casing 415 may include a plurality of openings 420 so that any leaking fluid will quickly contact the leak detector 405.

As shown in FIG. 4, the leak detector 405 may be disposed in the lower housing portion 210. The leak detector 405 and accompanying leak detector casing 415 may be disposed along and/or abut one or more internal edges 425a-425c, so that the leak detector extends at least partially around a perimeter of the lower housing portion 210. As described above, leaks may develop in one or more areas of the machine 100, 200, for example, from the fluid lines 125, the cartridge 115, fluid bags, and the like. It is advantageous to dispose the leak detector 405 along the internal edges 425a-425c of the lower housing portion 210, as the leaked fluid migrates towards the bottom, internal edges 425a-425d of the housing 105, 205. In embodiments where the warmer pouch 305 is insertable in the machine 200 (FIGS. 3A-3C), a heating plate or other internal heating system for adjusting the temperature of the warmer pouch may be disposed in the cavity 410 above the leak detector 405. Additionally, being disposed in the lowermost portion of the housing 105, 205 ensures that any fluid that may drip or gather is immediately detected. This ensures a rapid detection of any fluid leaks. Other locations of a leak detector, and more than one leak detector, may be contemplated within a housing, e.g., dedicated to a particular potential source of leaking, so as to bring the leak detector into closer proximity to that source and thus hasten any leak detection at that source.

Figure 5A:
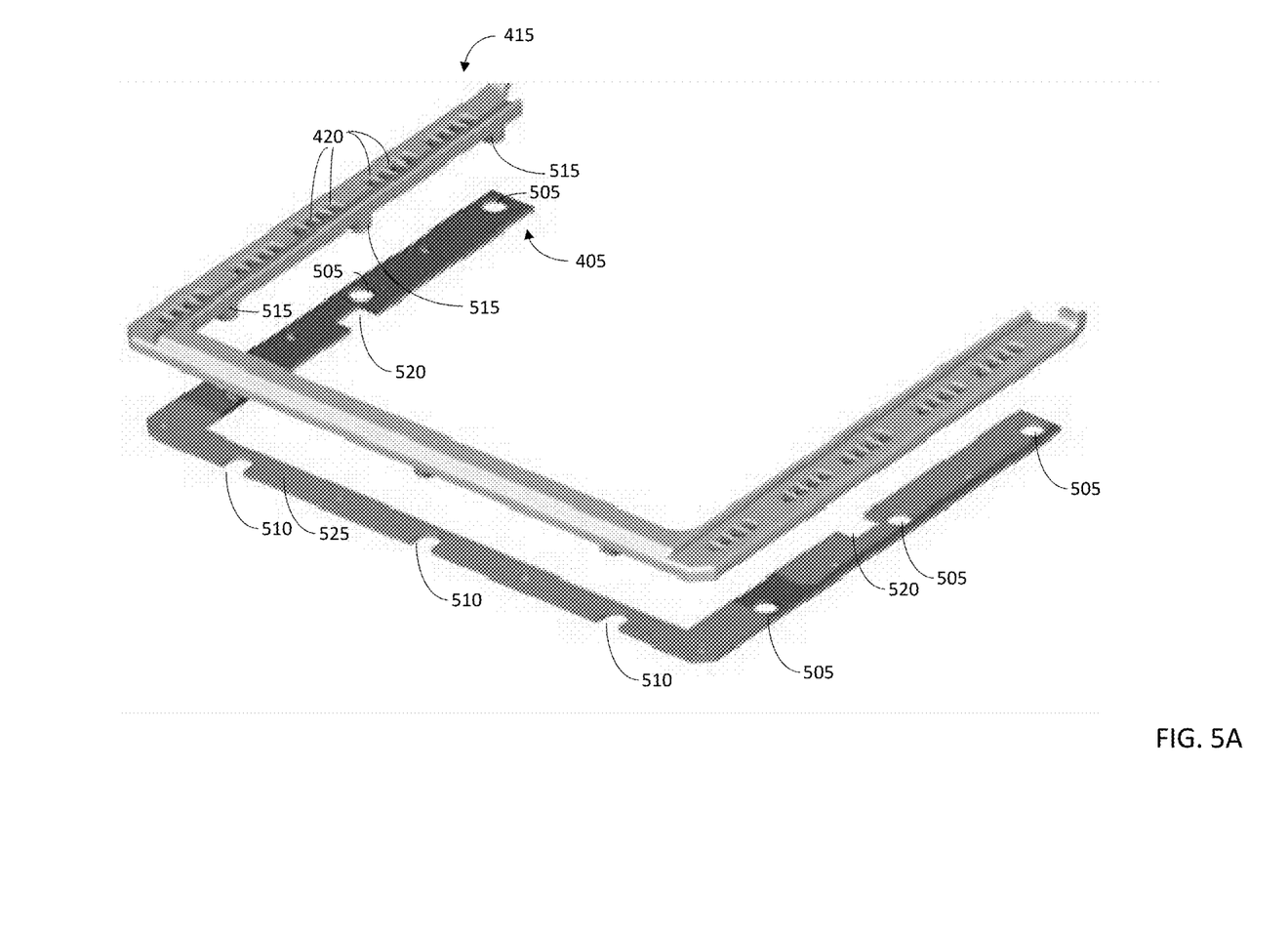
FIGS. 5A-5B illustrate a leak detector according to an embodiment of the present disclosure.
Figure 5B:
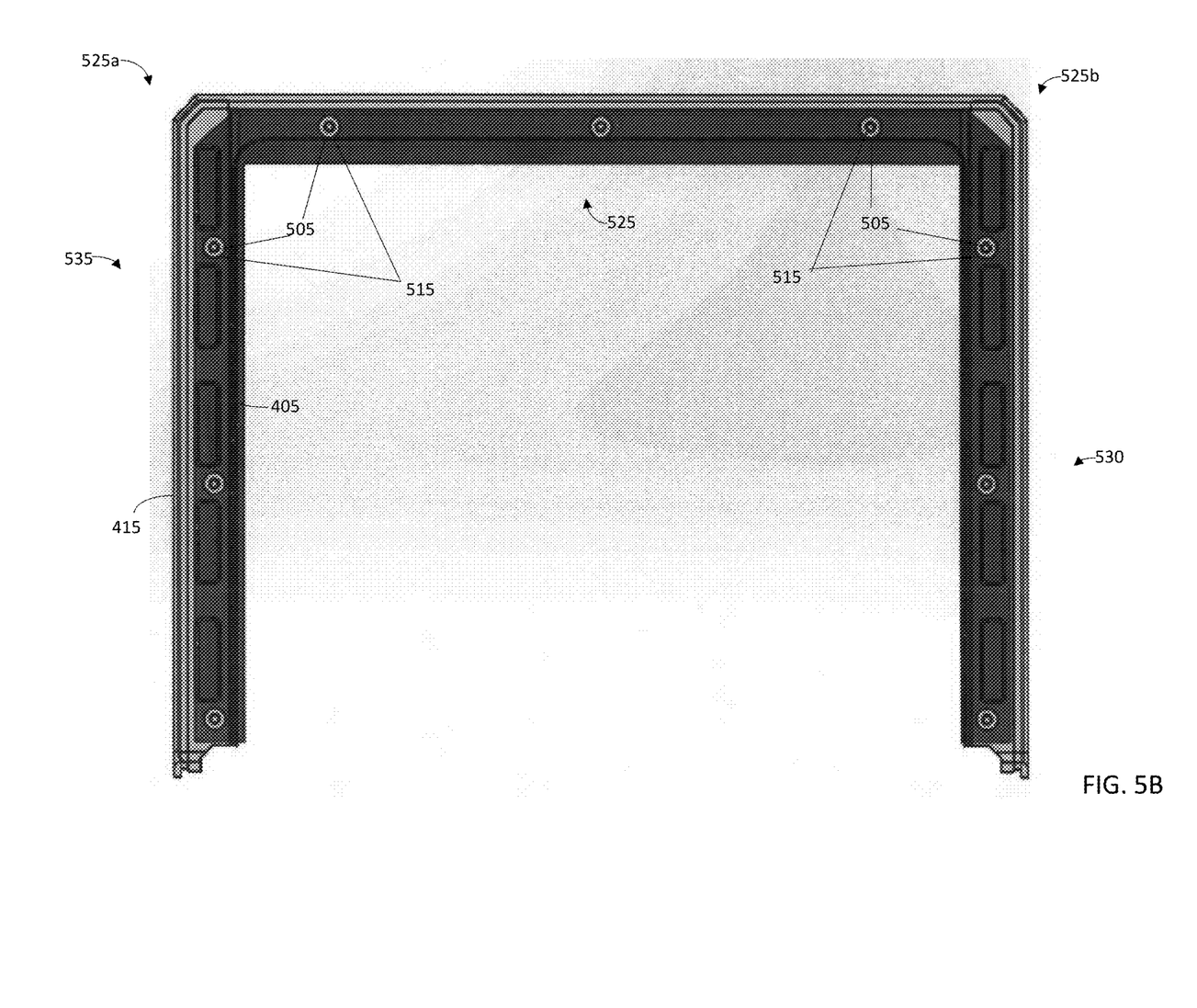

The leak detector 405 may be fixedly coupled to at least one of the lower housing portion 210 and the leak detector casing 415. In embodiments, the leak detector 405 may include a plurality of apertures 505 and cutouts 510. At least one of the plurality of apertures 505 and cutouts 510 may receive a corresponding protrusion 515 on the leak detector casing 415. The protrusion 515 may be configured to extend through a respective aperture 505 and/or cutout 510 for at least partial insertion into a corresponding hole 430 in the lower housing portion 210. It is understood that the apertures 505 and/or cutouts 510, protrusions 515 and holes 430 may be aligned for assembly and joining. Although the leak detector 405 and leak detector casing 415 may be coupled to the lower housing portion 210 via protrusions 515 through apertures 505 and/or cutouts 510 and holes 430, it is not critical and any known joining mechanisms may be used, including but not limited to pins, solder beads, weld beads, and the like. In some embodiments, the leak detector 405 may include one or more notches 520 for alignment with alignment pins 435 on the lower housing portion 210.

According to an exemplary embodiment illustrated in FIGS. 5A-5B, the leak detector 405 and the leak detector casing 415 may be formed in a U- or C-shape, including a first portion 525 having a first end 525a and a second end 525b, a second portion 530 extending from one of the first end 525a or the second end 525b, and a third portion 535 extending from the other of the first end 525a or the second end 525b. The second portion 530 and the third portion 535 may be substantially parallel to each other and substantially perpendicular to the first portion 525. The leak detector casing 415 may be integrally formed in some embodiments, and in other embodiments, the first portion 525 may be coupled to the second portion 530 and the third portion 535 at the first and second ends 525a, 525b, respectively. The first, second, and third portions 525, 530, 535 may be coupled together by known mechanical fasteners, screws, press fit, welding, soldering, adhesives, tongue and groove connections, and the like. It is understood though that the leak detector may be located and include any other shape and configuration in accordance with the requirements or other application of the machine 100, 200, so long as the circuit is situated to be contacted by any source of undesired fluid present in the machine to short the circuit and signal a leak.

Figure 6A:
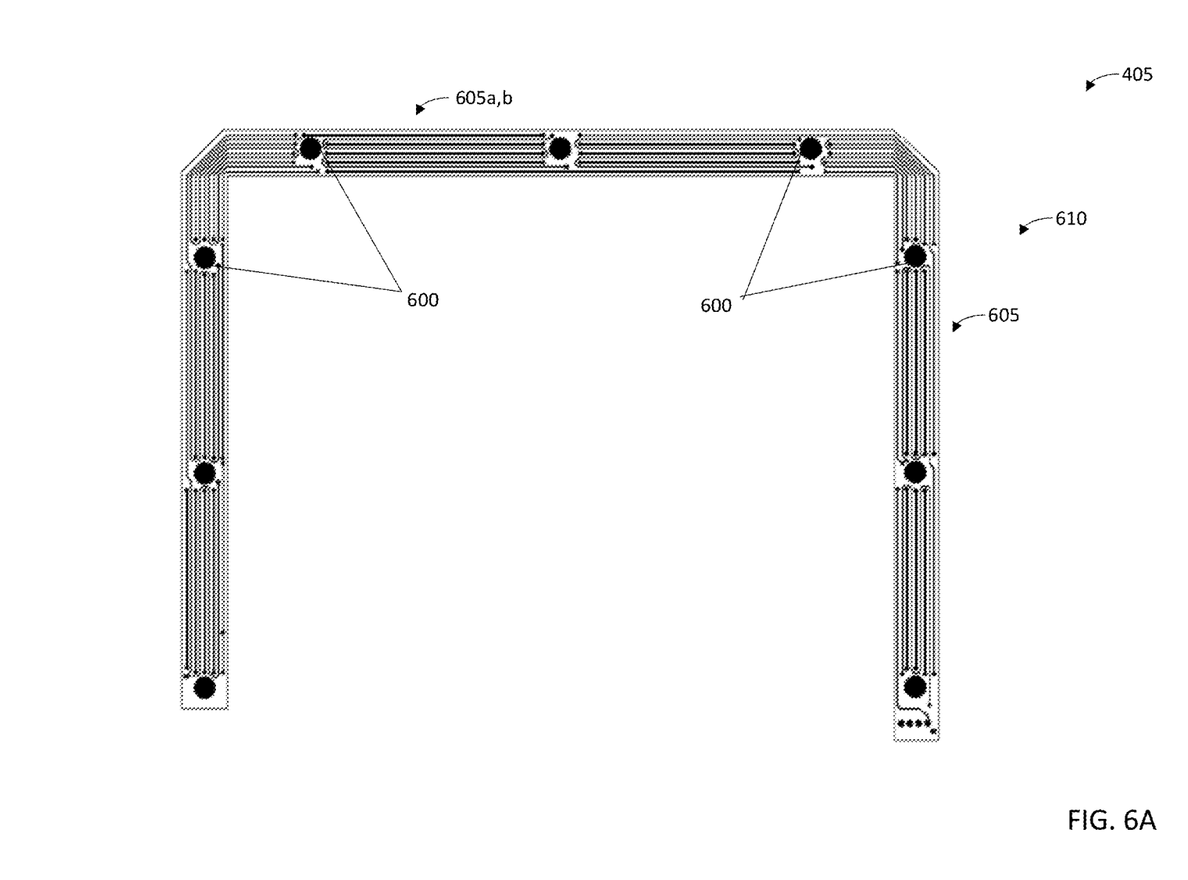
FIGS. 6A-6B illustrate an electrical circuit according to an embodiment of the present disclosure.
Figure 6B:
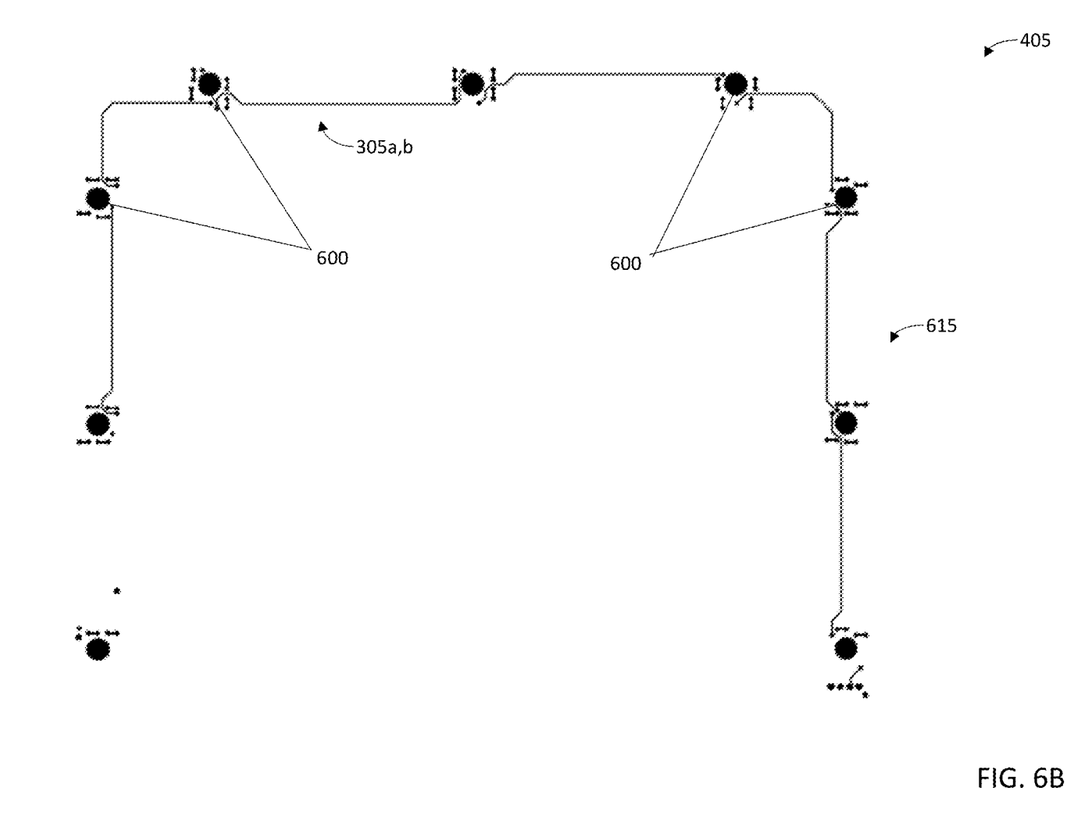

As shown in FIGS. 6A, 6B, the flexible circuit of the leak detector 405 may include conductive circuits 605 with a plurality of pads 600 and positive and negative traces 605a, 605b. The positive and negative traces 605a, 605b may extend along at least one of the front side 610 and the back side 615 of the circuit 605 adjacent and substantially parallel to each other. The positive and negative traces 605a, 605b may extend along in a direction parallel to the first portion 525, the second portion 530, and the third portion 535, for example, in a C- or U-shape.

The leak detector 405 may be electrically connected in the machine 200, for current to flow along the path of the positive and negative traces 605a, 605b during operation. For example, in the event of a leak, fluid contacting the leak detector causes a short of the electrical circuit. A cable connection from the leak detector 405 to a main circuit board may provide current and allow for constant monitoring of a short of the leak detector 405. In embodiments, the machine 100, 200 may monitor and/or react to the short circuit condition of the leak detector 405. For example, a signal may be sent to the user interface portion 130, 230 to indicate the leak, and/or an audio audible or a light indicator may be triggered. The machine 100, 200 may automatically shut off operation, or allow the user to monitor, pause, and/or cease the dialysis operation based on the leak detection. The leak detector 405 may be resettable or replaceable, in that when fluid is not present the controller may allow for normal operation of the machine 100, 200. In other embodiments, in the event of a leak and the electrical circuit of the leak detector 405 shorts, the machine 100, 200 may no longer be operable, requiring replacement of the entire machine. This may be advantageous to ensure that only dialysis machines operating at the highest quality of care for patients are in use.

As described above, the leak detector 405 may be disposed in an area of the machine 100, 200 so any leaked fluid may contact the flexible circuit. For example, fresh dialysate, spent dialysate, waste, warmer fluid and/or excess fluid may leak in the machine 100, 200. During normal operation of the dialysis machine 100, 200, all fluid is properly contained within its respective fluid bags and/or fluid lines. The leak detector 405 may be configured to monitor the machine 100, 200 through all stages of operation to ensure patient safety. In the event of fluid contacting the leak detector and a short occurring, the machine 100, 200 may be configured to react to the short circuit condition of the leak detector 405 in any number of ways, including initiating alarms and/or causing one or more operational conditions.

Figure 7:
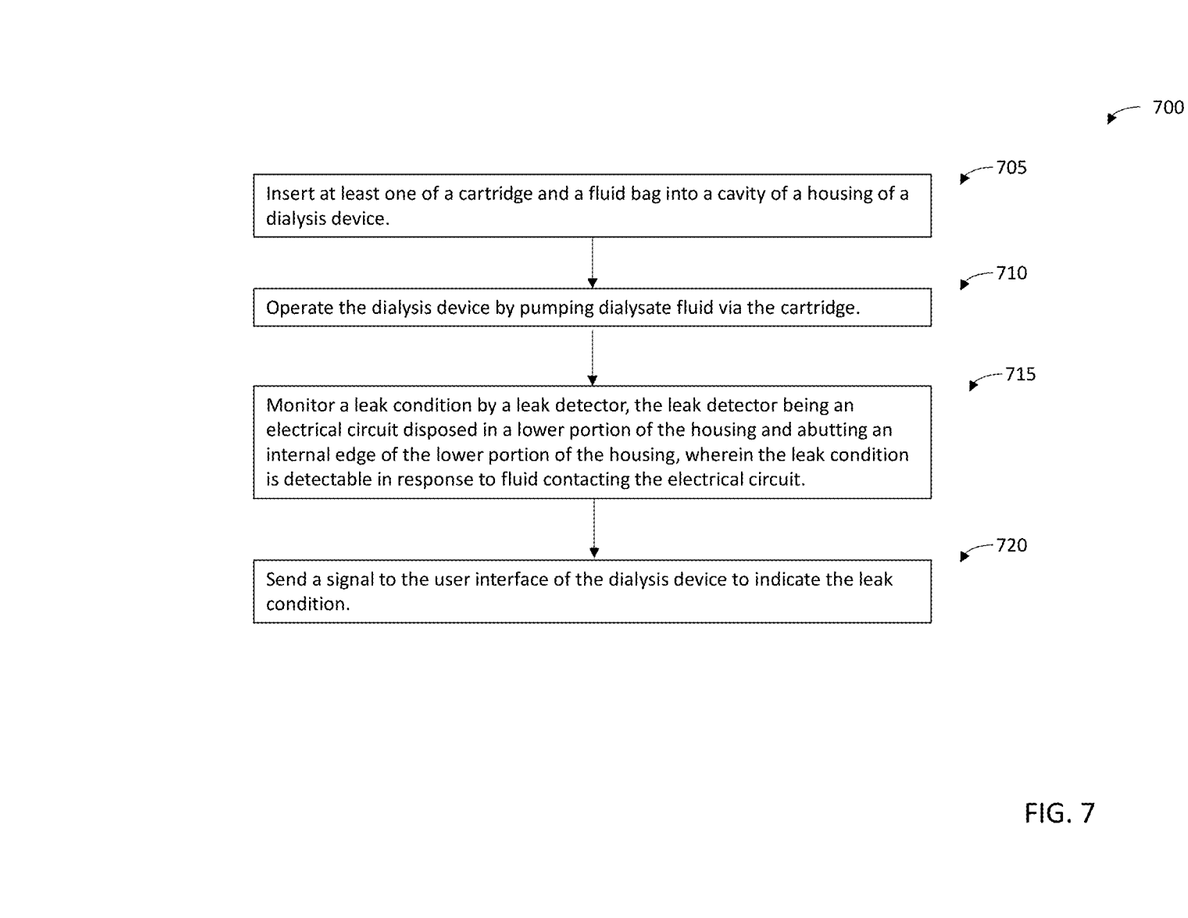
FIG. 7 illustrates a flow diagram of a method of detecting a leak in a dialysis machine according to an embodiment of the present disclosure.

Referring now to FIG. 7, a flow diagram 700 of a method of detecting a leak during a dialysis operation according to an embodiment of the present invention is shown. At step 705, components of the dialysis machine 100, 200 are inserted, for example, a cartridge 115 may inserted into a cavity 120 of a housing 105 of the dialysis machine 100, and/or fluid bags, such as warmer pouch 305, may be inserted in the gap 220 of the lower housing portion 210 of the machine 200. At step 710, the dialysis machine 100, 200 is operated by pumping dialysate fluid via the cartridge 115 or other fluid component or source. As described above, in a peritoneal dialysis operation, fresh dialysate may be pumped into an abdomen of a patient, and spent dialysate, including waste and excess fluid, may flow out of the patient's abdomen. At step 715, a leak condition of the dialysis machine 100, 200 is monitored by the leak detector 405. The leak detector 405 may be an at least partially flexible circuit disposed in a lower portion 210 of the housing 105, 205. At step 720, when a leak is detected in the dialysis machine 100, 200, an electrical short of the leak detector 405 occurs by fluid contacting the electrical circuit, thereby sending a signal to the user interface portion 130, 230 of the machine 100, 200 to indicate the leak condition. As described above, the machine 100, 200 may send an audible or a visual indication of the leak condition, and alternatively or additionally automatically stop dialysis operation.

Some embodiments of the disclosed system may be implemented, for example, using a storage medium, a computer-readable medium or an article of manufacture which may store an instruction or a set of instructions that, if executed by a machine (i.e., processor or microcontroller), may cause the machine to perform a method and/or operations in accordance with embodiments of the disclosure. In addition, a server or database server may include machine readable media configured to store machine executable program instructions. Such a machine may include, for example, any suitable processing platform, computing platform, computing device, processing device, computing system, processing system, computer, processor, or the like, and may be implemented using any suitable combination of hardware, software, firmware, or a combination thereof and utilized in systems, subsystems, components, or sub-components thereof. The computer-readable medium or article may include, for example, any suitable type of memory unit, memory device, memory article, memory medium, storage device, storage article, storage medium and/or storage unit, for example, memory (including non-transitory memory), removable or non-removable media, erasable or non-erasable media, writeable or re-writeable media, digital or analog media, hard disk, floppy disk, Compact Disk Read Only Memory (CD-ROM), Compact Disk Recordable (CD-R), Compact Disk Rewriteable (CD-RW), optical disk, magnetic media, magneto-optical media, removable memory cards or disks, various types of Digital Versatile Disk (DVD), a tape, a cassette, or the like. The instructions may include any suitable type of code, such as source code, compiled code, interpreted code, executable code, static code, dynamic code, encrypted code, and the like, implemented using any suitable high-level, low-level, object-oriented, visual, compiled and/or interpreted programming language.

As used herein, an element or operation recited in the singular and proceeded with the word "a" or "an" should be understood as not excluding plural elements or operations, unless such exclusion is explicitly recited. Furthermore, references to "one embodiment" of the present disclosure are not intended to be interpreted as excluding the existence of additional embodiments that also incorporate the recited features.

While the systems and techniques described herein for detecting leaks have been largely explained with reference to a dialysis machine, in particular, a peritoneal dialysis machine, the systems and techniques described for detecting leaks may be used in connection with other types of medical treatment systems and/or machines, such as a hemodialysis machine or other medical treatment device involving medical fluids. In some implementations, the dialysis machine may be configured for use in a patient's home (e.g., a home dialysis machine). The home dialysis machine can take the form of a peritoneal dialysis machine or a home hemodialysis machine.

The present disclosure is not to be limited in scope by the specific embodiments described herein. Indeed, other various embodiments of and modifications to the present disclosure, in addition to those described herein, will be apparent to those of ordinary skill in the art from the foregoing description and accompanying drawings. Thus, such other embodiments and modifications are intended to fall within the scope of the present disclosure. Furthermore, although the present disclosure has been described herein in the context of a particular implementation in a particular environment for a particular purpose, those of ordinary skill in the art will recognize that its usefulness is not limited thereto and that the present disclosure may be beneficially implemented in any number of environments for any number of purposes. Accordingly, the claims set forth below should be construed in view of the full breadth and spirit of the present disclosure as described herein.

What is claimed is:
1. A dialysis machine, comprising:
a housing including an outer periphery surface and an elongated slot formed in the outer periphery surface;
an internal heating system including a heating element disposed in the housing;
a warmer pouch insertable into the elongated slot, the warmer pouch being operatively coupled to first fluid flow lines so that fluid is moved through the warmer pouch and warmed using the heating element when the warmer pouch is positioned in the elongated slot formed in the housing; and a leak detector disposed in the elongated slot of the housing, the leak detector being arranged and configured to at least partially surround the internal heating system in the housing;

wherein in response to fluid contacting the leak detector, a leak in the dialysis machine is detectable.

2. The dialysis machine of claim 1, wherein upon detection of the leak, the dialysis machine is configured to send a signal to indicate the leak.

3. The dialysis machine of claim 2, wherein the signal is sent to at least one of a user interface of the dialysis machine, a remote location, and generates an alarm condition.

4. The dialysis machine of claim 3, wherein the alarm condition generates one of an audio audible or a light indicator.

5. The dialysis machine of claim 2, wherein the signal automatically shuts off operation of the dialysis machine.

6. The dialysis machine of claim 1, wherein the housing includes an upper housing portion and a lower housing portion collectively defining the outer periphery surface, the elongated slot being positioned between the upper and lower housing portions.

7. The dialysis machine of claim 6, wherein the leak detector abuts an internal edge of the lower housing portion.

8. The dialysis machine of claim 1, wherein the leak detector is an electrical circuit, the electrical circuit being at least partially covered by a leak detector casing.

9. The dialysis machine of claim 8, wherein the leak detector casing includes a plurality of openings.

10. The dialysis machine of claim 8, wherein the leak detector is coupled to at least one of the leak detector casing and the housing of the dialysis machine.

11. The dialysis machine of claim 1, wherein the elongated slot and the leak detector are substantially U- or C-shaped such that the elongated slot and the leak detector extend across a front surface of the housing and along at least a portion of the side surfaces of the housing.

12. The dialysis machine of claim 11, wherein the leak detector includes a first portion, a second portion disposed at a first end of the first portion, and a third portion disposed at a second end of the first portion opposite of the first end.

13. The dialysis machine of claim 12, wherein the first portion is substantially perpendicular to the second portion and the third portion and the second portion is substantially parallel to the third portion.

14. A dialysis machine, comprising:
a housing including an outer periphery surface, an elongated slot formed in the outer periphery surface, and a cavity;
an internal heating system including a heating element disposed in the housing;
a warmer pouch insertable into the elongated slot, the warmer pouch being operatively coupled to first fluid flow lines so that fluid is moved through the warmer pouch and warmed using the heating element when the warmer pouch is positioned in the elongated slot formed in the housing;
a cartridge insertable into the cavity, the cartridge being operatively coupled to second fluid flow lines and the warmer pouch so that fluid is moved through the cartridge and between the cartridge and the warmer pouch when the cartridge is positioned in the cavity formed in the housing; and
a leak detector disposed in the elongated slot of the housing, the leak detector being arranged and configured to at least partially surround the internal heating system in the housing;
wherein in response to fluid contacting the leak detector, a leak in the dialysis machine is detectable.

15. The dialysis system of claim 14, wherein upon detection of the leak, the dialysis machine is configured to send a signal to indicate the leak.

16. The dialysis system of claim 15, wherein the signal is sent to at least one of a user interface of the dialysis machine, a remote location, and generates an alarm condition.

17. The dialysis system of claim 16, wherein the alarm condition generates one of an audio audible or a light indicator.

18. The dialysis system of claim 15, wherein the signal automatically shuts off operation of the dialysis machine.

19. The dialysis system of claim 14, wherein the leak detector is an electrical circuit.

* * * * *